United States Patent [19]
Barrows

[11] 4,360,013
[45] Nov. 23, 1982

[54] POLYMERIC ACID CONTRACEPTIVE DEVICES

[75] Inventor: Thomas H. Barrows, Cottage Grove, Minn.

[73] Assignee: Minnesota Mining and Manufacturing Company, St. Paul, Minn.

[21] Appl. No.: 142,239

[22] Filed: Apr. 21, 1980

[51] Int. Cl.³ ............................ C08J 9/16; A61F 5/46; B01D 47/16; B32B 5/18
[52] U.S. Cl. ................................. 128/130; 128/260; 128/132 R; 128/270; 424/DIG. 14
[58] Field of Search ........... 128/270, 271, 130, 132 R, 128/138 R, 260; 424/DIG. 4; 536/85, 3

[56] References Cited
U.S. PATENT DOCUMENTS

| | | | |
|---|---|---|---|
| 3,067,745 | 12/1962 | Burgeni et al. | 128/270 |
| 3,433,225 | 3/1969 | Voss et al. | 128/270 |
| 3,865,108 | 2/1975 | Hartop | 128/270 |
| 3,916,898 | 11/1975 | Robinson | 128/270 |
| 4,274,410 | 6/1981 | Chvapil | 128/270 |

OTHER PUBLICATIONS

Am. Pharm. Ass., Handbook of Nonprescription Drugs, 5th ed., pp. 201–208.

*Primary Examiner*—V. Millin
*Assistant Examiner*—Nancy A. B. Swisher
*Attorney, Agent, or Firm*—Cruzan Alexander; Donald M. Sell; Lorraine R. Sherman

[57] ABSTRACT

A disposable non-woven sponge vaginal contraceptive device is made of alginic acid or related polysaccharides bearing carboxylic acid functionality and a method of making same is disclosed.

17 Claims, 4 Drawing Figures

POLYMERIC ACID CONTRACEPTIVE DEVICES

TECHNICAL FIELD

The present invention relates to a disposable nonwoven sponge vaginal contraceptive device particularly suited as a chemical and mechanical barrier to the passage of sperm into the female uterine cavity.

BACKGROUND ART

Due to increasing concern about the side effects of oral contraceptives and IUD's, there is renewed interest in barrier contraceptives by health care providers, government regulatory officials and consumers. Barrier methods of contraception have been in scientific eclipse for almost two decades but there has been a recent shift of interest back to these traditional methods of fertility regulation.

The prior art is replete with intravaginal materials useful as contraceptives and medicaments. The goal in these contraceptive methods has been to provide an effective, efficient and convenient means of preventing sperm from reaching the cervical uterine canal. The normal vagina maintains an acid pH of from 4 to 5 and in this environment spermatozoa have motility and viability for a relatively short period of time, i.e. about 1 to 2 hours. On the other hand, sperm maintain their motility and viability in the uterine cervix for up to 48 hours. The objective of all barrier contraception is to prevent sperm from entering the uterine cervix and subsequently fertilizing an ovum in the fallopian tube.

The diaphragm was introduced by an English pharmacist, Mensinga, in the 1880's. Used alone or in conjunction with spermicidal cream, foam, suppository preparation or jelly, it can be an effective contraceptive device when used correctly and consistently. Creams, foams, suppositories and jellies alone statistically provide less protection against unwanted pregnancies. All of the aforementioned contraceptive methods have inherent deficiencies: they tend to interfere with the coital act due to their relatively short duration of effectiveness, and a high level of motivation is required for their correct and consistent usage. Thus, any invention that provides a more convenient or longer acting vaginal contraceptive method would represent a significant improvement in the state of the art.

The active agent found in many of the current spermicidal preparations is a nonionic surfactant such as nonylphenoxypoly(ethyleneoxy)ethanol, also known as nonoxynol-9, or p-diisobutylphenoxypolyethoxyethanol. Other agents known to be effective include bactericides such as benzethonium chloride, chemically known as N,N-dimethyl-N-[2-[2-[4-(1,1,3,3-tetramethylbutyl)-phenoxy]ethoxy]ethyl]benzenemethanaminium chloride, phenyl mercuric acetate, and acids such as boric acid and tartaric acid.

Several approaches to providing vaginal contraceptive methods with improved duration of effectiveness have been reported in the literature. For example, U.S. Pat. Nos. 3,991,760, 3,995,633, 3,995,634, 4,031,202 and 4,073,833 disclose intravaginal devices that continuously release nonionic surfactant to create a spermicidal environment within the vagina. A serious disadvantage of these approaches is that the surfactant is delivered to the vagina constantly whether needed or not. Thus, the woman is exposed to a much higher level of surfactant than with devices such as the diaphragm and cream or jelly intended for intermittent-use. Since creams or jellies occasionally produce irritation such as a burning sensation, the continuous-release approach is certain to worsen this problem. Moreover, it has recently been reported that nonoxynol-9 is capable of being absorbed into the bloodstream through the vaginal mucosa. This fact suggests that continuous administration of spermicidal surfactants may not provide the same degree of toxicological safety as intermittent administration.

Barrier contraceptive sponges are known in the prior art. U.S. Pat. No. 3,762,414 describes an improved configuration of a rubber sponge for contraceptive use and Republic of South Africa Pat. No. 767,523 describes a sponge made from collagen.

Vaginal contraceptives that rely on an acid pH are also well known in the prior art. Indeed, the historical contraceptive use of rose hips and lemons which are characteristically of low pH is known. U.S. Pat. No. 4,027,670 discloses a contraceptive device containing a contraceptive gel. The gel includes citric acid and has a pH of approximately 2. U.S. Pat. No. 2,149,240 and U.S. Pat. No. 2,330,846 disclose acid vaginal preparations useful as contraceptives. However, such preparations are not residual.

Fibrous materials are well known for their use as tampons and are disclosed in U.S. Pat. Nos. 2,202,566, 3,067,743, 3,067,745 and 4,186,742. The latter discloses a medicated tampon in the form of a soft porous foam ball made of polyurethane, polyester and polyether materials and impregnated with antibiotic and contraceptive agents for the control of venereal disease and pregnancy.

U.S. Pat. No. 3,545,439 discloses polymeric vaginal rings for releasing medicaments and spermicidal preparations.

Some of the natural and synthetic polymers in acid form have known spermicidal activity. U.S. Pat. No. 2,851,453 discloses an acid carboxymethyl-cellulose preparation used in a tablet. However, a tablet has limited residual effect and is inconvenient to use.

Alginate polymers based on alginic acid salts have previously been used in vaginal preparations and are disclosed in U.S. Pat. No. 3,067,743. The patentee describes the use of an alginate fiber in the formulation of spermicidal preparations. In this case, however, the alginate was used solely as a carrier for spermicidal agents such as quinine or dioctyl sulphosuccinate and any excess alginic acid was converted to soluble sodium or ammonium alginate by neutralization. This preparation does not provide long-acting spermicidal protection nor was any residual alginic acid reported in the compositions.

U.S. Pat. No. 3,653,383 describes a water-absorbent and water-disintegrative open-celled porous sponge made by freeze-drying a gel of sodium and calcium alginate. Such a sponge would not be useful for vaginal contraception since the alginic acid is present only in the nonacidic salt form.

U.S. Pat. No. 4,187,286 discloses a suppository contraceptive containing a spermicidally-active ingredient and in addition alginic acid; the purpose of the alginic acid (present in a proportion of about 13.5–16.5 weight percent) is to form carbon dioxide by neutralization reaction with sodium bicarbonate and as an additional thickening agent in neutral form.

DISCLOSURE OF THE INVENTION

The present invention relates to the use of alginic acid or related polysaccharides bearing carboxylic acid functionality in the form of an intravaginal contraceptive device. These polysaccharides may be natural or semi-synthetic materials. The intravaginal contraceptive device comprises a sponge which itself is the spermicidal material, said material being useful with or without additional inert fibrous materials. As used herein, sponge refers to a resilient non-woven web of interconnecting, partially interconnecting or non-interconnecting fibers containing open and/or closed cells of air. The disposable intravaginal contraceptive device may be inserted into the upper vault of the vagina proximal to the cervix without professional assistance, remains in position without regard to the activity of the user and may be easily removed by the user by means of a string attached to the device. As used herein, string means a soft natural or synthetic fiber cord, loop or ribbon. The intravaginal contraceptive device is highly absorbent and will rapidly absorb liquid, including ejaculate. It is capable of maintaining its efficacy while remaining in position in the vagina for several days. The acid materials are not continuously released in the normally acid vaginal environment. To be effective, the device must remain in position for at least one hour after intercourse takes place.

Useful acidic polymers of the present invention include alginic acid, polymannuronic acid, polyguluronic acid, polygalacturonic acid, polyglucuronic acid, and other polymeric hexuronic acids. These polymers can be blended with or grafted onto inert polymers such as cellulose, or cellulose can be converted to a spermicidally active agent by synthetic modification to introduce carboxylic acid functionality.

Alginic acid is especially useful since it is readily available, inexpensive, and well recognized as safe for pharmaceutical applications. In addition, alginic acid can be prepared in fiber form or converted to alginic acid fibers from alginate salts and blended with synthetic fibers. A further advantage of alginic acid is that unlike other acids used as spermicides, alginic acid is essentially insoluble in an acidic environment such as in the human vagina. Thus, the activity remains at the site of application where it is needed most. This provides for long-lasting protection since the alginic acid is consumed only to the extent that alkaline secretions, such as semen, are present to dissolve it.

The contraceptive devices of the present invention are made of highly resilient materials, have prompt and large fluid-binding capacity, are easily inserted and removed and appear to be non-irritating in contact with vaginal tissue. They can be conveniently fabricated to be of such size that the cervical os will be covered. It is advantageous that the contraceptive device is bulky enough so that if not properly inserted into the upper vault of the vagina, its mechanical presence will be noted by either the male or female.

BRIEF DESCRIPTION OF THE DRAWINGS

In the accompanying diagrammatic drawings which illustrate the invention.

DETAILED DESCRIPTION OF THE INVENTION

The present invention relates to a disposable, resilient contraceptive device for insertion into the upper vault of the vagina proximal to the cervix comprising a cylindrical, absorbent non-woven sponge of alginic acid or related polysaccharide fibers bearing carboxylic acid functionality and a retrieval means.

Figure 1:
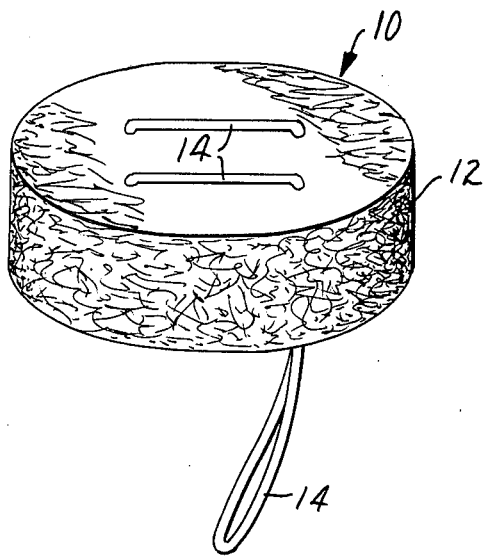
FIG. 1 is a perspective view of a vaginal device according to the present invention.

Referring now more particularly to the drawings, FIG. 1 shows a non-woven sponge vaginal contraceptive device 10 of one layer 12, of cylindrical shape and bearing a soft natural or synthetic fiber string 14 laced therethrough, said string being useful for the removal of the device from the vaginal canal after use. The contraceptive device 10 of FIG. 1 is of such dimensions as to completely cover the female cervical os and of sufficient thickness (at least 0.5 cm) to be an effective spermicidal dose for at least one coital act. It is preferable for maximum effectiveness that the dry contraceptive device have a density of at least 10 mg/cc. Density as used herein refers to the weight per unit volume of sponge including the weight of air in that volume.

Figure 2:
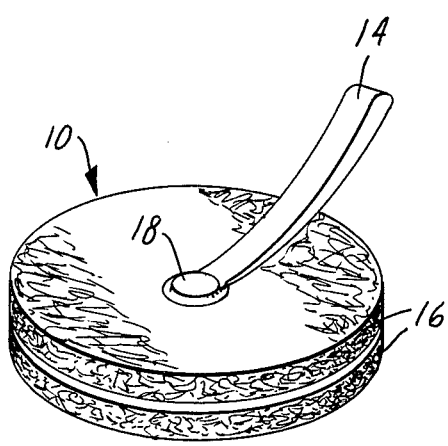
FIG. 2 is a perspective view of a multilayer embodiment of the present invention viewed from the bottom thereof.

In the embodiment illustrated in FIG. 2, device 10 has a plurality of layers 16 of acidic, non-woven sponge material bearing a soft synthetic fiber string 14 attached securely to the contraceptive device by a sonic weld 18.

Figure 3:
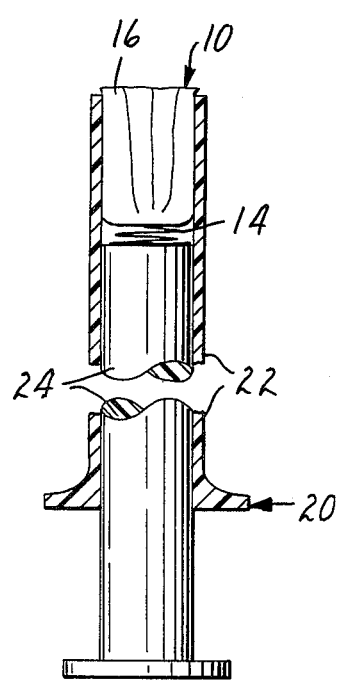
FIG. 3 is a sectional view of a syringe-type applicator containing the folded vaginal device in its distal end.

FIG. 3 is a sectional view of a syringe-type applicator 20 comprising a hollow barrel 22 and a concentric plunger 24 with contraceptive device 10 folded in the distal end of the applicator. The applicator and contraceptive device as shown are ready for insertion into the vaginal canal.

Figure 4:
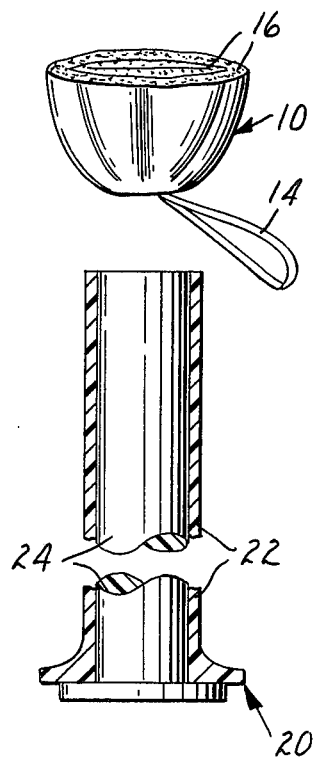
FIG. 4 is a sectional view of a syringe-type applicator and vaginal device as it would appear immediately after expulsion of the device from the applicator.

FIG. 4 shows a sectional view of applicator 20 and contraceptive device 10 of FIG. 3 as they would appear after insertion into the upper vault of the vaginal canal. The plunger 24 fills the barrle 22 and the device 10 has been expelled from the applicator 20. The contraceptive device 10, being resilient, immediately springs open to assume the shape as shown in either FIG. 1 or 2.

The sponge non-woven fibrous web of the present invention may be formed by airlaid processes well known in the art. See, for example, Example 1 in U.S. Pat. No. 4,059,114. Alginic acid fiber is preferably blended with an inert fiber to provide resiliency. Fibers of inert polymers suitable for blending are formed from nylons, polyesters, polyolefins and cellulosics. Preferred airlaid acidified webs of the present invention comprise 25% to 75% alginic acid fiber or related polysaccharide fibers bearing carboxylic acid functionality and 75% to 25% inert fibers. When the contraceptive device is suspended in 50 ml of distilled water it is preferable that sufficient acidic material be present so that the pH of the water is 2 to 4.

The invention is further illustrated by the following non-limiting examples.

As shown in the Examples below, the data in support of the utility disclosed herein for alginic acid and related polysaccharides bearing carboxylic functionality is based on in vivo safety tests in rabbits (Example 1), and in vitro spermicidal activity tests using both human sperm (Examples 1, 4, 5 and 6) and rabbit sperm (Examples 1-5 and 7).

EXAMPLE 1

Fabrication of a Binder Coated Non-Woven Web of Blended Alginic Acid and Polyester Staple Three kilograms of 3.8 cm, 1.8 denier calcium alginate staple (Kanga Hospital Products, Coventry, England) and 3 kilograms of 3.8 cm, 3.0 denier Fortrel polyester staple (Celanese Corporation of America) were machine blended and formed into a continuous 30.5 cm wide airlaid web. The denier of the bulk alginate or related fibers and additional fibrous materials should be low, between 1.5 and 18, preferably the major portion of the material being between 1.5 and 3.0. A low denier gives a high surface area and, hence, best spermicidal efficiency. Coarser fibers may be added to improve resiliency. The web was coated with a mixture prepared from the following components:

A. 2,360 g acrylate binder (Rhoplex HA-8, Rohm & Haas) in 11,760 g water
B. 43 g anionic surfactant (Tamol T731, Rohm & Haas) and 21 g nonionic surfactant (Triton X-100, Rohm & Haas) in 179 g water
C. 260 g thickener (Acrysol ASE60, Rohm & Haas) in 286 g water
D. 50 g 15 N Ammonium Hydroxide in 50 g Water The component mixtures A, B, C and D were combined at room temperature by stirring together, with the ammonia mixture being added last. Both sides of the web were coated using a wipe-film roll coater at the rate of about 3.5 mg/cm$^2$. This provided a unifying binder coating which bound the fibers together on the surface and, hence, defined the shape of the two surfaces. The coated web was deposited on release paper, carried on a conveyor belt through an oven maintained at a constant temperature of 123° C. until dry, and automatically wound up into large rolls to be acidified and used as needed.

Five 24 cm diameter circles of coated web were cut from the roll and placed in a large Buchner funnel with 5 liters of 1 N hydrochloric acid and allowed to soak for one hour. The acid solution was removed by suction and the product rinsed twice with 2 liter portions of water. The circular webs of calcium alginate thus converted to alginic acid were allowed to dry completely. Titration indicated that these samples contained 37% alginic acid. It was evident that some of the alginate was lost due to its conversion to a fine powder during the airlaying process.

In Vitro Human Spermicidal Activity Evaluation

Twenty 8×8 cm squares cut from the roll and acidifed as above, weighing approximately 1.5 g each, were tested using separate ejaculates from 20 different men with one total ejaculate being used per sample of test material. Each semen specimen was first examined for sperm concentration, percent motility, forward progression and volume. Results are tabulated in TABLE I. Each sample of test material was moistened with 0.9% sodium chloride solution, freed of excess solution by wringing, and placed in good contact with the semen specimen for 40 seconds by blotting the semen specimen with the sample of test material. The semen was generally well absorbed by the test material. Spermatozoa in the fluid recovered by squeezing the sample (referred to as "Absorbed Fluid" in TABLE I) were examined under the microscope and in each case found to be completely nonmotile. "Remaining Seminal Fluid" (TABLE I) refers to the very small amount of fluid that remained in the container when the sample of test material was removed 40 seconds after addition to the semen sample. Some motile spermatozoa remained in the "Remaining Seminal Fluid" because these had not come in contact with the test material.

Since alginic acid reacts with semen and hence is "used up" when utilized as a contraceptive device, the test material was analyzed and it was found that 500 mg (i.e., 0.5 g) of alginic acid fiber per coital act should be an effective dose considering the biological variability of semen alkalinity and volume. Thus, a contraceptive device which is 37% alginic acid should weigh at least 1.35 g.

TABLE I
RESULTS OF
IN VITRO HUMAN SPERMICIDAL ACTIVITY EVALUATION

| Sample No. | Volume (ml) | Sperm Conc. (× 10$^6$/ml) | Before | | Absorbed Fluid | | Remaining Seminal Fluid | |
|---|---|---|---|---|---|---|---|---|
| | | | % Motile | Forward Progression* (0-4) | % Motile | Forward Progression* (0-4) | % Motile | Forward Progression* (0-4) |
| 1 | 1.2 | 11 | 80 | +4 | 0 | — | 45 | +1 |
| 2 | 5.3 | 56 | 90 | +4 | 0 | — | 0 | — |
| 3 | 5.5 | 35 | 68 | +1 | 0 | — | 0 | — |
| 4 | 1.5 | 50 | 90 | +4 | 0 | — | 0 | — |
| 5 | 1.1 | 42 | 86 | +4 | 0 | — | 60 | +1 |
| 6 | 4.6 | 44 | 74 | +4 | 0 | — | 40 | +2 |
| 7 | 5.7 | 102 | 80 | +4 | 0 | — | 55 | +2 |
| 8 | 1.0 | 240 | 72 | +4 | 0 | — | 50 | +1 |
| 9 | 5.2 | 29 | 66 | +4 | 0 | — | 0 | — |
| 10 | 3.6 | 125 | 75 | +4 | 0 | — | 25 | +1 |
| 11 | 5.3 | 97 | 90 | +4 | 0 | — | 2 | 0 |
| 12 | 2.4 | 47 | 70 | +3 | 0 | — | 60 | +1 |
| 13 | 2.7 | 112 | 65 | +4 | 0 | — | 8 | +2 |
| 14 | 1.2 | 80 | 88 | +4 | 0 | — | 1 | 0 |
| 15 | 4.7 | 153 | 85 | +4 | 0 | — | 24 | 0 |
| 16 | 5.6 | 119 | 92 | +4 | 0 | — | 64 | +2 |
| 17 | 3.7 | 46 | 89 | +4 | 0 | — | 48 | +2 |
| 18 | 2.6 | 66 | 56 | +3 | 0 | — | 0 | — |
| 19 | 3.1 | 115 | 83 | +4 | 0 | — | 65 | +3 |

TABLE I-continued
RESULTS OF IN VITRO HUMAN SPERMICIDAL ACTIVITY EVALUATION

| Sample No. | Volume (ml) | Sperm Conc. ($\times 10^6$/ml) | Before | | Absorbed Fluid | | Remaining Seminal Fluid | |
|---|---|---|---|---|---|---|---|---|
| | | | % Motile | Forward Progression* (0–4) | % Motile | Forward Progression* (0–4) | % Motile | Forward Progression* (0–4) |
| 20 | 3.7 | 110 | 78 | +4 | 0 | — | 23 | +2 |

*scale used
— means forward progression cannot be evaluated because there is no motility
0 means no forward progression of sperm that are motile
1 to 4 indicates relative rate of forward progression with +4 being the maximum rate of forward progression

Evaluation of Vaginal Irritation Potential of Coated Alginic Acid-Polyester Web in Rabbits A 1.5 mm wide continuous sonic stitch was placed in samples of the above alginic acid-Fortrel polyester coated web by the use of a Branson Model 4120, 1250 watt, sonic welding machine equipped with a titanium horn and rotating anvil. The sonic stitch tacked the surfaces together to prevent escape of fibers from between the two coated surfaces. Control samples containing all of the ingredients except alginic acid were prepared and stitched in the same manner. Strips of test and control material approximately 5×18 mm were obtained by cutting on both sides of the stitch line.

Thirty-nine young female New Zealand White rabbits were used in this test. A laparotomy was performed on fifteen rabbits. The test material was then inserted by isolating the vagina and inserting the material through the vulva into the vagina. The test material was sutured in place with one 6-0 polypropylene stitch through the proximal vaginal wall and the inserted test material. Fifteen of the rabbits received samples of control material described in the previous paragraph, and nine rabbits were given a sham operation. The animals were sacrificed after 3, 7 and 14 days post operation and the condition of the vaginal tissue was evaluated visually and histologically. There was no visual evidence of irritation and microscopic evidence of vaginitis was infrequent and distributed among all three groups.

Effect of Acidity on the Viability of Rabbit Sperm

Although the acidity of alginic acid is an important factor in causing sperm death, this factor is apparently not the only mechanism of activity. Rabbit semen was acidified with physiological saline solution containing hydrochloric acid and cell death determined by use of a "live-dead" stain. The percent of dead sperm that were also decapitated—indicating severe cell disruption—was also recorded. The results of this test at various pH values were compared to the results obtained by contacting rabbit semen with the alginic acid-polyester blend sponge materials from the samples described above. The results, shown in TABLE II, clearly indicate that alginic acid is unexpectedly more potent as a spermicide than anticipated on the basis of its acid strength.

TABLE II
Effect of Acidity on the Viability of Rabbit Sperm

| Acid | pH | Live | Dead | % of Dead Decapitated |
|---|---|---|---|---|
| None (control) | 7.15 | 81% | 19% | 0 |
| Hydrochloric | 3.98 | 27% | 73% | 12 |
| Hydrochloric | 2.97 | 19% | 81% | 28 |
| Hydrochloric | 2.42 | 16% | 84% | 36 |
| Alginic | 2.52 | 0% | 100% | 90 |

EXAMPLE 2
Fabrication of Alginic Acid Sponge

A 2.0% solution of sodium alginate (Sigma Chemical Co.) was prepared by adding a slurry of 10.0 g sodium alginate in 20 ml of ethanol to 500 ml of water with rapid mechanical mixing. Mixing was continued for about 30 minutes to obtain a smooth, viscous solution. The solution was poured into polystyrene dishes and frozen at −20° C. The frozen discs were removed from the dishes and dried thoroughly by sublimation under high vacuum (0.1 Torr).

The freeze-dried discs were then soaked in 3 N HCl overnight and rinsed exhaustively with water. At this point the sponge properties were evident and the material could be wrung out without disintegrating. The final pH of the sponges was approximately 3.5. Drying was accomplished by soaking in alcohol followed by soaking in ether and then placing in a well ventilated area.

The following data is typical for a sample of sponge cut from a disc fabricated by this method:

| | |
|---|---|
| Sample Size | = 1 cm × 2.2 cm × 0.3 cm |
| Density | = 121 mg/cc |
| Absorbency ($gH_2O$/g Sponge) | = 23.5 |
| Percent Swell in $H_2O$ | = 172 |
| Water Absorption Rate | = 0.35 ml/sec |

In Vitro Evaluation of Spermicidal Activity Utilizing Alginic Acid Sponges

Freshly ejaculated semen collected from Dutch Belted rabbits was used. The test consists of pipetting exactly 0.5 ml of rabbit semen onto a 25 mg sample of sponge moistened with 0.9% NaCl solution, and after a few seconds, pressing the sponge on a microscope slide, covering with a cover glass, and viewing the sperm in the sample at 400× under phase contrast. The total time from initial contact of semen with the sponge to viewing the effects was no longer than 35 seconds in each case.

The alginic acid sponge produced 100% immobilization of sperm. In addition, the vast majority of sperm were decapitated, i.e., the heads were detached from the midpiece and tail segments.

Two control materials were used: Ivalon (formaldehyde crosslinked polyvinyl alcohol, Unipoint Industries), a commercial synthetic surgical sponge, and freeze-dried collagen (Sigma Chemical Company). Neither of these materials produced any deleterious effect on sperm motility.

EXAMPLE 3

Synthesis of Cellulose Succinate 25 g of microcrystalline cellulose (J. T. Baker Chemical Company), 25 g of succinic anhydride, and 200 ml of pyridine were combined in a 500 ml round bottom flask and heated in a water bath at 45° C. with stirring overnight. A portion of the resultant suspension was centrifuged and the gelatinous sediment collected after decantation and resuspended in ethanol. The product was again collected by centrifugation and washed by successive resuspension and centrifugation several times each in ethanol, 0.01 N HCl, distilled water, and ethanol, and dried under vacuum.

The dried product was easily ground to a powder with mortar and pestle. The infrared spectrum exhibited a strong absorption band at 1730 cm$^{-1}$ which was absent in the spectrum of the cellulose starting material, thus indicating the presence of carboxylic acid functionality. It is believed that the chemical modification (i.e., introduction of carboxylic acid functionality) was primarily confined to the surface of the cellulose particles, the core being unmodified cellulose.

In Vitro Evaluation of Spermicidal Activity of Cellulose Succinate

Suspensions of the material to be tested were prepared in 0.9% NaCl solution. Equal volumes (0.2 ml) of test suspension and freshly ejaculated Dutch Belted rabbit semen were rapidly mixed by stirring and a small drop of the mixtured placed on a microscope slide, covered with a cover glass, and the sperm in the sample viewed at 400× under phase contrast. The time elapsed between mixing and visualization was no greater than 45 seconds.

A 15% suspension of cellulose succinate (pH=approx. 3.0) gave 100% immobilization of all sperm with a significant incidence of decapitation.

Control materials used are as follows:

1. Microcrystalline cellulose (J. T. Baker Chemical Company), 25% (pH=approx. 4.5). No appreciable effect on sperm motility.
2. Amberlite IRC-50 ion-exchange resin with carboxylic functionality (Mallinckrodt Chemical Works), 10% (pH=approx. 3.0) ball milled to a fine powder. There was slight adverse effect on sperm motility (e.g., decreased forward progression with some immobilization). A 10% suspension was used due to the fine particle size which obstructed vision of the sperm at higher weight concentrations.

EXAMPLE 4

Polygalacturonic Acid

Polygalacturonic acid is also useful since it can be obtained by de-esterification of pectin which is readily available. Polygalacturonic acid powder (Eastman Organic Chemicals) was suspended in 0.9% sodium chloride (15% weight/volume) and evaluated by the same method described in Example 3 using both rabbit and human semen specimens. The polygalacturonic acid gave virtually instantaneous sperm immobilization in both cases.

EXAMPLE 5

Oxidized Cellulose

Two commercial preparations of cellulose made acidic by partial oxidation were tested for spermicidal activity as in Example 3. These materials, sold as surgical hemostatic agents, are Oxycel (oxidized cellulose-fibrous material, Parke-Davis) and Surgicel (oxidized cellulose-woven fabric, Surgikos). Both samples exhibited spermicidal activity.

EXAMPLE 6

Fabrication of a Thermally Bonded Sponge Web of Blended Bicomponent Polyolefin and Alginic Acid Two hundred grams of 3.8 cm, 1.8 denier calcium alginate staple (Kanga Hospital Products, Coventry, England) and 180 grams of 3.0 denier, 6.4 cm bicomponent polyolefin staple (Chisso ES Fiber, Chisso Corp., Osaka, Japan) were machine blended and formed into a continuous 30.5 cm wide airlaid web. The web was passed through an oven at 142° C. for a period of less than 2 minutes which caused the polyolefin fibers to bond to each other, entrapping the alginate fibers and forming a stable sponge product 2.0 cm thick and having a density of 12 mg/cc.

Fifty squares, 3.8×3.8 cm, were cut from the bonded web. Half of these were placed in 2 liters of 1 N hydrochloric acid and the other half, as a control, were placed in 2 liters of distilled water. After soaking for one hour, the two batches of sponges were separately collected on a Buchner funnel, rinsed several times with distilled water, and allowed to dry. The process of soaking and drying increased the sponge density to 20 mg/cc for the alginic acid web and 30 mg/cc for the calcium alginate web. A sample of acidic sponge titrated at 2.24 meq./g with pKa=3.4. Since unblended alginic acid fiber titrates at 4.5 meq./g, the acidic sponge contained approximately 50% alginic acid.

The sponges were cut into samples measuring 1.0 cm×3.5 cm diameter for use in the following in vitro spermicidal activity test.

In Vitro Evaluation of Spermicidal Activity of Bicomponent Polyolefin-Alginic Acid Sponge A fresh, human semen specimen was checked for normalcy as in Example 1 and then divided into two equal volumes of approximately 1.5 ml each. Each portion of semen was placed in the center of separate Petri dishes. One control sponge and one test sponge described above were moistened with 0.9% saline solution and each used to absorb a semen specimen by blotting. After no more than 30 seconds, each sponge was pressed against a microscope slide and the fluid thus transfered covered with a cover glass and examined at 400×. Sperm obtained from the calcium alginate-containing control sponge were still highly motile whereas sperm obtained from the alginic acid-containing test sponge were completely immobilized.

EXAMPLE 7

Effect of Calcium Content on the Spermicidal Property of Alginic Acid Fiber

A blend of 3.8 cm, 1.8 denier calcium alginate staple (Kanga Hospital Products, Coventry, England) and 3.8 cm, 3.0 denier Dacron polyester staple (DuPont) was prepared in a manner similar to that of Example 1. This sample contained approximately 44% calcium alginate. Four 1.5 g portions of this material were evaluated after first soaking three of them in 1 N hydrochloric acid for different lengths of time, rinsing with distilled water, drying, and reweighing. The samples were then remoistened with distilled water and the pH estimated by means of test paper (Hydrion Papers, Micro Essential Laboratory, New York).

Samples of pure, unblended calcium alginate were also soaked in 1 N hydrochloric acid, rinsed, dried, reweighed, and pH estimated in the same manner after the sample were moistened with distilled water. These samples were assayed for calcium content by the atomic absorption method.

Fresh semen obtained from Dutch Belted rabbits was absorbed into a portion of each of the distilled water moistened samples. After no more than 40 seconds, each sample was pressed on a microscope slide and the sperm in the fluid this transferred viewed at 400× under phase contrast. The results are summarized in TABLE III.

TABLE III

SPERMICIDAL PROPERTY of BLENDED and UNBLENDED ALGINATE ACID FIBERS with VARYING CALCIUM CONTENT

| | Leaching Time (min.) in 1N HCl | | | |
|---|---|---|---|---|
| | 0 | 5 | 15 | 30 |
| Blend Wt. Loss | — | 11.2% | 11.7% | 12.4% |
| Alginate Wt. Loss | — | 25.3% | 26.5% | 28.0% |
| Blend pH | 6.4 | 3.0 | 3.0 | 3.0 |
| Alginate pH | 6.0 | 2.5 | 2.5 | 2.5 |
| Calcium Content of Alginate (ppm) | 23,000 | 1,800 | 1,100 | 980 |
| Spermicidal Effect of Alginate | None | Complete | Complete | Complete |
| Spermicidal Effect of Blend | None | Incomplete | Incomplete | Complete |

Although rabbit sperm are somewhat more resistant to immobilization by acid than human sperm, all of the acidified calcium alginate samples caused total, instantaneous immobilization. The blended samples, however, provide a lower density of alginate thus giving a slightly higher pH and providing a more severe test of spermicidal efficacy. In this case the alginate with the lowest calcium content gave the best spermicidal results at approximately equivalent pH, thus demonstrating the superiority of the almost fully acidified form of alginic acid over its partially acidified salt forms as an active agent.

What is claimed is:

1. A disposable, resilient contraceptive device for insertion into the upper vault of the vagina proximal to the cervix comprising a cylindrical, absorbent non-woven sponge of alginic acid or related polysaccharide fibers bearing carboxylic acid functionality in an effective spermicidal quantity and a retrieval means.

2. A contraceptive device according to claim 1 wherein the retrieval means is a soft natural or synthetic fiber string attached thereto.

3. A contraceptive device according to claim 1 wherein said sponge includes additional inert fibrous materials blended therein.

4. A contraceptive device according to claim 3 wherein the additional inert fibrous material is a polyester staple.

5. A contraceptive device according to claim 3 wherein the additional inert fibrous material is a thermo-bonded bicomponent polyolefin staple.

6. A contraceptive device according to claim 3 wherein the fibrous materials have a denier in the range of 1.5–18.0.

7. A contraceptive device according to claim 3 wherein the fibrous materials have a denier in the range of 1.5–3.0.

8. A contraceptive device according to claim 1 wherein the sponge is coated with a unifying binder coating.

9. A contraceptive device according to claim 1 having a dry sponge density of at least 10 mg/cc.

10. A contraceptive device according to claim 1 wherein the device suspended in 50 ml of distilled water has a pH of 2 to 4.

11. A contraceptive device according to claim 1 wherein the sponge is at least 0.5 cm. thick.

12. A contraceptive device according to claim 1 wherein the diameter of the sponge is of sufficient size to completely cover the female cervical os.

13. A contraceptive device according to claim 1 wherein the sponge is a single layer.

14. A contraceptive device according to claim 1 wherein the sponge comprises a plurality of layers.

15. A contraceptive device according to claim 1 wherein the device contains at least 0.5 g by weight of alginic acid.

16. A method of preventing conception in a female human comprising
    (a) inserting a contraceptive device according to claim 1 into the upper vault of the vagina proximal to the cervix prior to intercourse and
    (b) maintaining said device in place at least 1 hour after intercourse takes place.

17. A disposable, resilient contraceptive device for insertion into the upper vault of the vagina proximal to the cervix comprising a cylindrical, absorbent, non-woven sponge of alginic acid in an effective spermicidal quantity and a retrieval means.

* * * * *